United States Patent
Fukushima et al.

(10) Patent No.: US 11,573,171 B2
(45) Date of Patent: Feb. 7, 2023

(54) OBSERVATION SYSTEM FOR ACQUIRING IMAGES OF CULTURE MEDIUM IN AT LEAST THREE COLORS

(71) Applicant: OLYMPUS CORPORATION, Tokyo (JP)

(72) Inventors: Ikutoshi Fukushima, Fuchu (JP); Shogo Usui, Machida (JP); Tsuyoshi Mochizuki, Musashino (JP); Masaru Mizunaka, Hino (JP); Shintaro Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/821,538

(22) Filed: Mar. 17, 2020

(65) Prior Publication Data
US 2020/0217782 A1    Jul. 9, 2020

Related U.S. Application Data

(63) Continuation of application No. PCT/JP2017/034326, filed on Sep. 22, 2017.

(51) Int. Cl.
*H04N 7/18* (2006.01)
*G01N 21/27* (2006.01)
(Continued)

(52) U.S. Cl.
CPC ........... *G01N 21/272* (2013.01); *C12M 23/22* (2013.01); *C12M 31/02* (2013.01); *C12M 41/06* (2013.01);
(Continued)

(58) Field of Classification Search
CPC ......... G01N 21/272; G01N 2015/1006; G01N 2015/0065; G01N 15/0612;
(Continued)

(56) References Cited

U.S. PATENT DOCUMENTS

2010/0060142 A1* 3/2010 Itou ................. B82Y 30/00
313/498
2010/0260422 A1* 10/2010 Ito .................... C12M 41/14
382/190
(Continued)

FOREIGN PATENT DOCUMENTS

JP    S62-115297 A    5/1987
JP    2009-152827 A    7/2009
(Continued)

OTHER PUBLICATIONS

English translation of International Preliminary Report on Patentability together with the Written Opinion from related International Application No. PCT/JP2017/034326 dated Mar. 24, 2020.
(Continued)

*Primary Examiner* — Eileen M Adams
(74) *Attorney, Agent, or Firm* — Scully, Scott, Murphy & Presser, P.C.

(57) ABSTRACT

An observation system includes an observation apparatus including a housing having an arrangement surface for placement of a sample, the sample including a culture medium, and an external illumination unit which is disposed outside the housing and includes at least one light source configured to emit illumination light. At least a part of the arrangement surface is formed of a transparent member having an optically transparent property. The observation apparatus includes an imaging unit which is provided in the housing and includes an image sensor configured to image, via the transparent member, the sample illuminated by the illumination light from the external illumination unit to acquire images of at least three colors.

20 Claims, 10 Drawing Sheets

(51) Int. Cl.
*G06T 7/90* (2017.01)
*H04N 9/04* (2006.01)
*C12M 1/00* (2006.01)
*C12M 1/34* (2006.01)
*G01N 21/25* (2006.01)
*G02B 21/06* (2006.01)
*G02B 21/36* (2006.01)
*G06T 7/00* (2017.01)
*H04N 5/225* (2006.01)

(52) U.S. Cl.
CPC ........... *C12M 41/26* (2013.01); *G01N 21/255* (2013.01); *G02B 21/06* (2013.01); *G02B 21/365* (2013.01); *G06T 7/0016* (2013.01); *G06T 7/90* (2017.01); *H04N 5/2256* (2013.01); *H04N 9/0451* (2018.08); *G06T 2207/10024* (2013.01); *G06T 2207/30024* (2013.01)

(58) Field of Classification Search
CPC ....... G01N 2015/1486; G01N 15/1463; G01N 21/80; G01N 2021/178; G01N 21/251; G01N 21/255; G06T 7/90; G06T 7/0016; G06T 2207/10024; G06T 2207/30024; H04N 9/0451; H04N 5/2256; G02B 21/361; G02B 21/362; G02B 21/082; G02B 21/06; G02B 21/365; C12M 41/36; C12M 23/22; C12M 31/02; C12M 41/06; C12M 41/26; G03B 15/00
USPC .......................................................... 348/135
See application file for complete search history.

(56) References Cited

U.S. PATENT DOCUMENTS

| | | | | |
|---|---|---|---|---|
| 2012/0214250 | A1* | 8/2012 | Oura | G01N 21/80 436/163 |
| 2013/0038727 | A1* | 2/2013 | Clark | C12M 41/46 348/143 |
| 2014/0113383 | A1* | 4/2014 | Jorgensen | H04N 5/2354 348/222.1 |
| 2015/0063675 | A1* | 3/2015 | Yan | G06T 7/001 382/141 |
| 2016/0006993 | A1* | 1/2016 | Kuramoto | H04N 5/232933 348/71 |

FOREIGN PATENT DOCUMENTS

| | | | |
|---|---|---|---|
| JP | 2010-273632 A | 12/2010 | |
| WO | WO-2005006943 A2 * | 1/2005 | ........... G02B 27/149 |
| WO | WO-2007022413 A2 * | 2/2007 | .............. G06T 7/90 |
| WO | WO 2008/129789 A1 | 10/2008 | |

OTHER PUBLICATIONS

International Search Report dated Dec. 19, 2017 issued in PCT/JP2017/034326.
Japanese Office Action dated Apr. 20, 2021 received in 2019-542915.

* cited by examiner

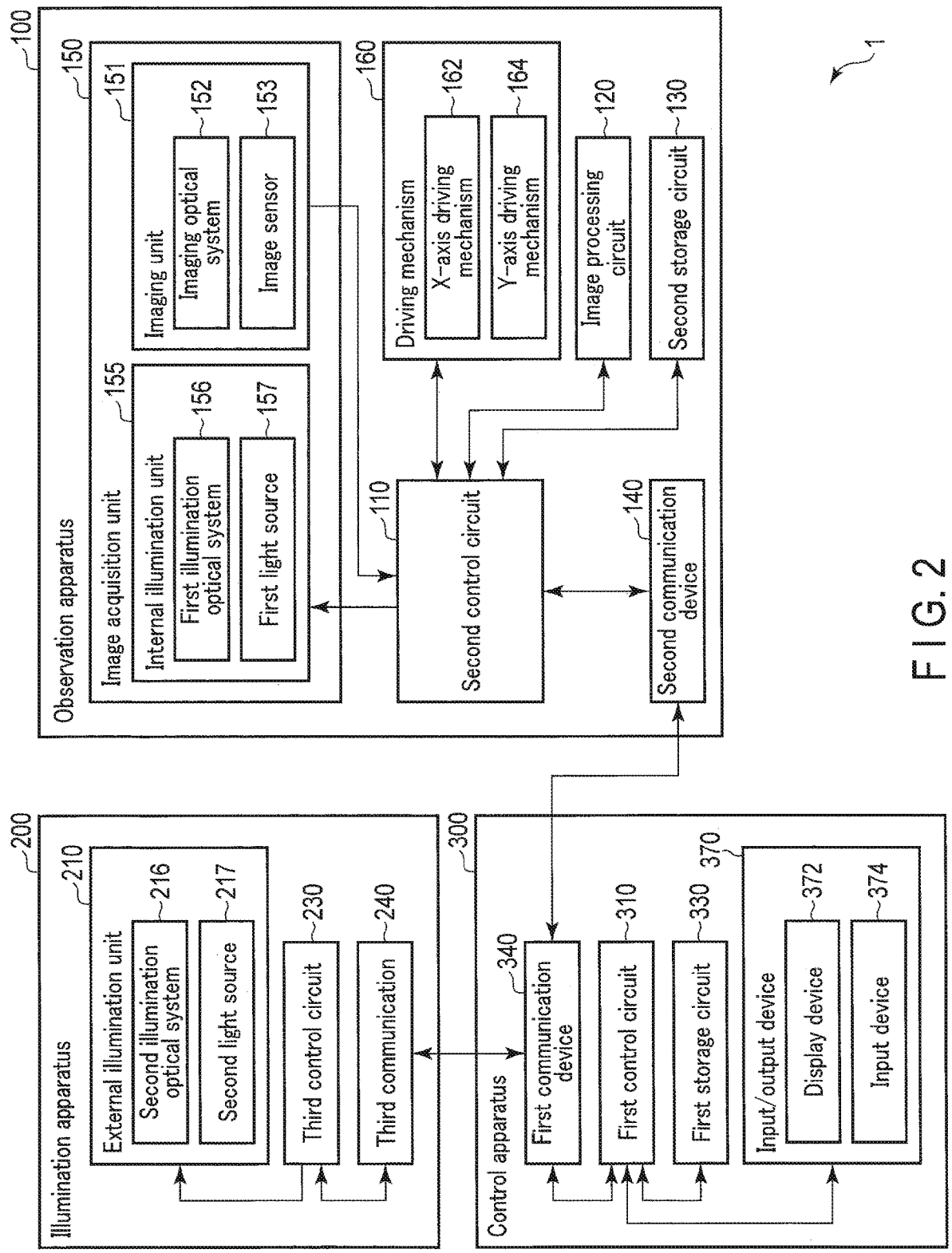
F I G. 2

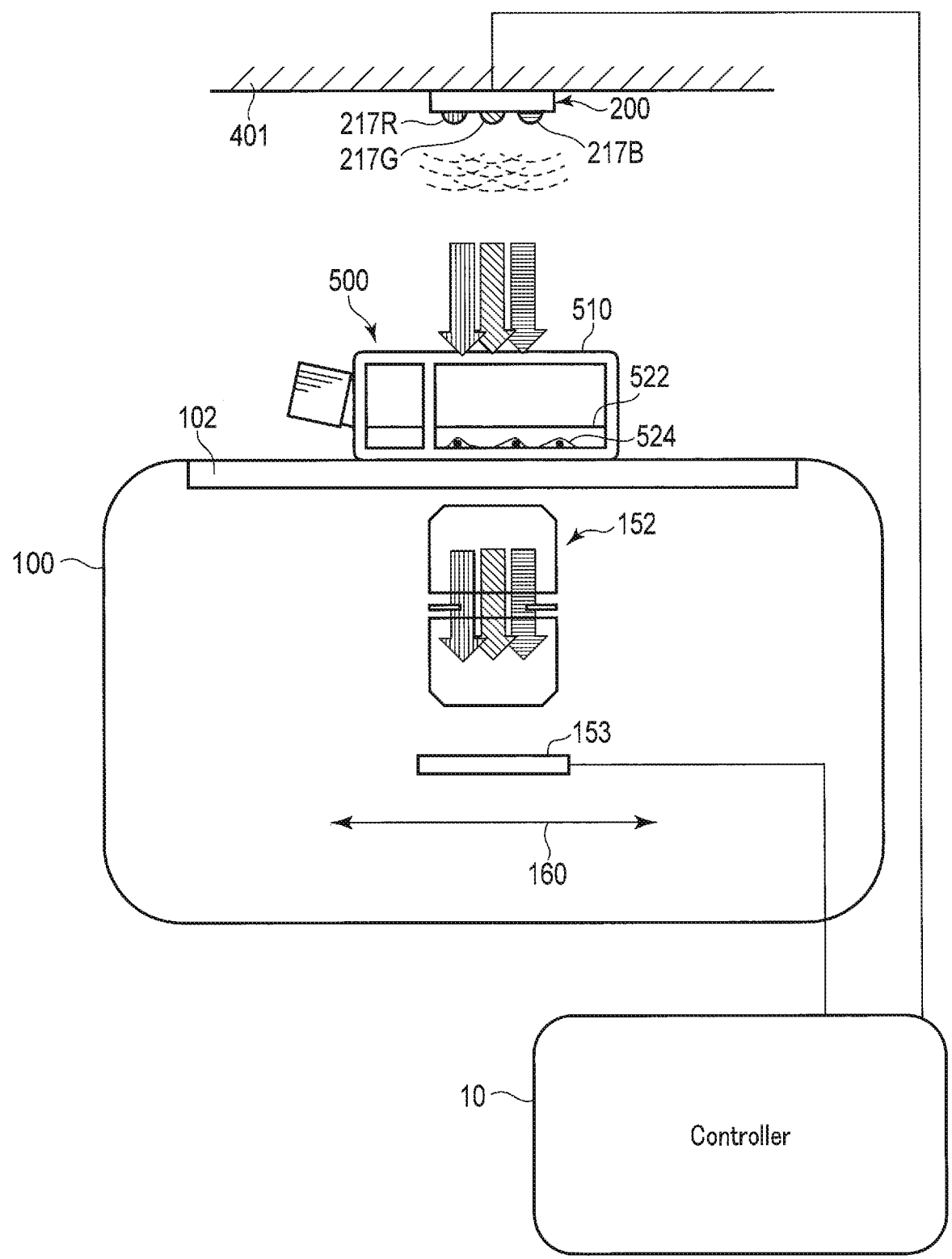
F I G. 5A

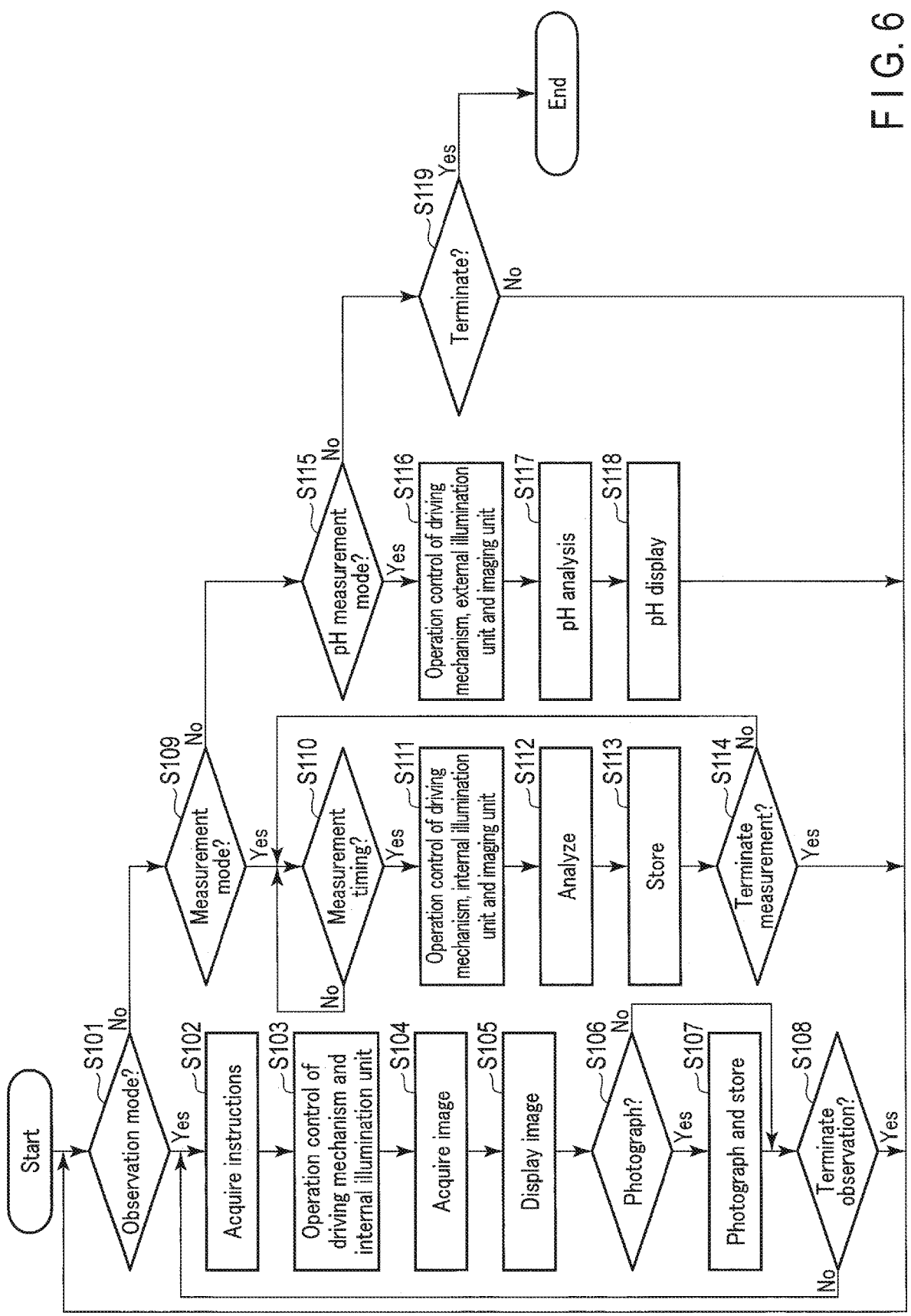
F I G. 6

OBSERVATION SYSTEM FOR ACQUIRING IMAGES OF CULTURE MEDIUM IN AT LEAST THREE COLORS

CROSS-REFERENCE TO RELATED APPLICATION

This is a Continuation Application of PCT Application No. PCT/JP2017/034326, filed Sep. 22, 2017, the entire contents of which are incorporated herein by reference.

BACKGROUND

The present invention relates generally to an observation system.

There is a demand to understand the state of cultured cells etc., when the cells etc. are cultured in an incubator. Thus, generally, a culture vessel is suitably taken out of the incubator and the cultured cells etc. are observed with a microscope. In addition, the pH of the culture medium is also of interest with regards to a state of the cultured cells. For example, US 2012/0214250 A1 discloses a pH measuring device capable of measuring the pH of the culture medium during cell culturing, and a special culture vessel for the measuring device.

SUMMARY

According to an exemplary embodiment, an observation system includes an observation apparatus including a housing having an arrangement surface for placement of a sample, the sample including a culture medium, and an external illumination unit which is disposed outside the housing and includes at least one light source configured to emit illumination light, wherein at least apart of the arrangement surface is formed of a transparent member having an optically transparent property, and the observation apparatus includes an imaging unit which is provided in the housing and includes an image sensor configured to image, via the transparent member, the sample illuminated by the illumination light from the external illumination unit to acquire images of at least three colors.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a block diagram schematically illustrating a configuration example of the observation system according to the one embodiment.

FIG. 5A is a diagram schematically illustrating an example of a variation of the configuration of the observation system according to the one embodiment.

FIG. 6 is a flowchart schematically illustrating an example of an operation of the observation system according to the one embodiment.

DETAILED DESCRIPTION

[Configuration of Observation System]
<Overview of Observation System>

Figure 1:
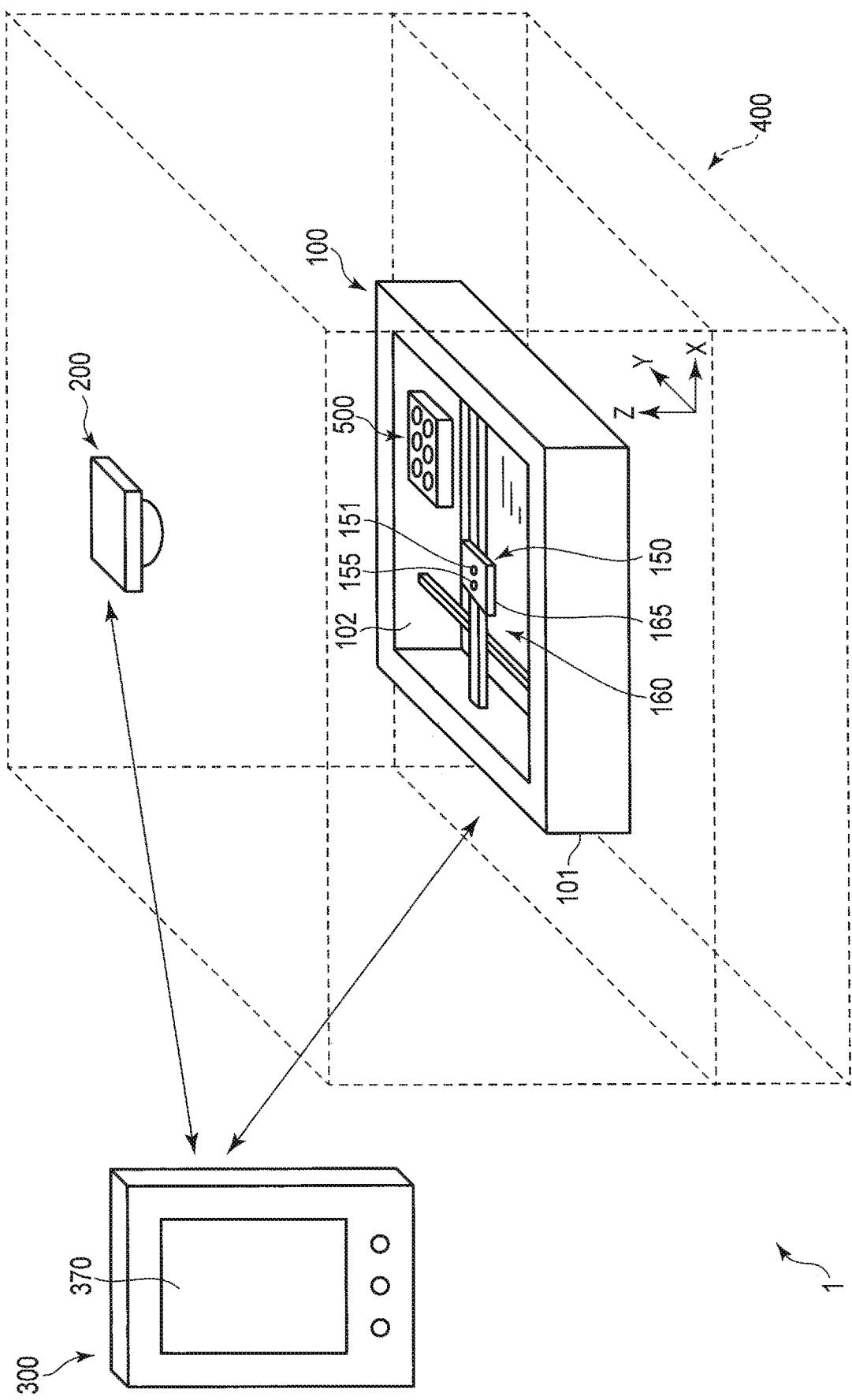
FIG. 1 is a diagram schematically illustrating a configuration example of an observation system according to one embodiment.

An observation system according to the present embodiment is a system for imaging cells, cell groups, tissues, and the like in culture, and storing and analyzing the number, morphology, and the like of the cells or cell groups. FIG. 1 is a schematic diagram showing a general appearance of the observation system 1. FIG. 2 is a block diagram schematically illustrating a configuration example of the observation system 1. The observation system 1 includes an observation apparatus 100, an illumination apparatus 200, and a control apparatus 300. The observation apparatus 100 has a substantially flat plate shape. A sample 500 to be observed is arranged on the upper surface of the observation apparatus 100, and the observation apparatus 100, the illumination apparatus 200, and the sample 500 are set, for example, inside an incubator 400. The incubator 400 is a general incubator for cell cultures. For the following description, an X axis and a Y axis that are orthogonal to each other are defined in a plane parallel to a plane on which the sample 500 of the observation apparatus 100 is disposed, and a Z axis is defined so as to be orthogonal to the X axis and the Y axis.

The observation apparatus 100 includes a housing 101, a transparent plate 102, and an image acquisition unit 150. The transparent plate 102 as a transparent member having optically transparent characteristics is arranged on at least a part of the upper surface of the housing 101. The image acquisition unit 150 is provided inside the housing 101. The image acquisition unit 150 includes an imaging unit 151, an internal illumination unit 155, and a support unit 165. As shown in FIG. 1, the internal illumination unit 155 is provided at the support unit 165. Further, the imaging unit 151 is provided near the internal illumination unit 155 of the support unit 165. The image acquisition unit 150 illuminates the sample 500 via the transparent plate 102, and captures an image of the sample 500.

The illumination apparatus 200 is provided in, for example, a ceiling portion inside the incubator 400. The image acquisition unit 150 of the observation apparatus 100 can also acquire an image of the sample 500 by using illumination light emitted from the illumination apparatus 200.

The control apparatus 300 is installed, for example, outside the incubator 400. The control apparatus 300 communicates with the observation apparatus 100 and communicates with the illumination apparatus 200. The control apparatus 300 transmits various instructions to the observation apparatus 100, and acquires and analyzes data obtained from the observation apparatus 100. Further, the control apparatus 300 transmits an instruction regarding the illumination state of the illumination apparatus 200 to the illumination apparatus 200.

The observation system 1 can image a broad extent of the sample 500 by repeatedly imaging it while moving the image acquisition unit 150 in the X-axis direction and the Y-axis direction in one observation operation. Further, the observation system 1 can repeatedly perform such an observation operation at intervals set according to a predetermined sequence.

<Sample>

The sample 500 to be measured by the observation system 1 is, for example, as follows. The sample 500 includes, for example, a vessel including a culture medium in which cells are being cultured. The culture vessel can be, for example, a petri dish, a culture flask, a multiwell plate, or the like. Thus, the shape, size, and the like of the vessel are not limited. The culture medium may be a liquid medium or a solid medium. The cells to be measured are, for example, cultured cells, which may be adherent cells or floating cells. The cells may be spheroids or tissues. Further, the cell may be derived from any organism, and may be a bacterium or the like. As described above, the sample 500 includes a biological sample that is an organism or a sample derived from the organism.

<Control Apparatus>

The control apparatus 300 controls the entire observation system 1. The control apparatus 300 is, for example, a personal computer (PC), a tablet-type information terminal, or the like. FIG. 1 illustrates a tablet-type information terminal.

The control apparatus 300 is provided with an input/output device 370 including a display device 372 such as a liquid crystal display and an input device 374 such as a touch panel. The input device 374 may include a switch, a dial, a keyboard, a mouse, and the like, in addition to the touch panel.

Further, the control apparatus 300 is provided with a first communication device 340. The first communication device 340 is a device for communicating with the observation apparatus 100 and the illumination apparatus 200. For this communication, wireless communication using, for example, Wi-Fi (registered trademark) or Bluetooth (registered trademark) is used. Further, wired communication may also be used. The control apparatus 300, the observation apparatus 100, and the illumination apparatus 200 may be connected to each other via a telecommunication line such as the Internet to communicate with each other.

Further, the control apparatus 300 includes a first control circuit 310 and a first storage circuit 330. The first control circuit 310 controls the operation of each unit of the control apparatus 300. The first storage circuit 330 stores programs and various parameters used in, e.g., the first control circuit 310. The first storage circuit 330 stores data obtained at the observation apparatus 100 and received from the observation apparatus 100.

The first control circuit 310 controls the operation of each unit of the control apparatus 300. The first control circuit 310 performs various arithmetic operations related to control for measurement of the sample 500, controls operation of the display device 372, controls storing of information in the first storage circuit 330, and controls communication with the observation apparatus 100 via the first communication device 340. In addition, the first control circuit 310 may perform various analyses based on the image acquired from the observation apparatus 100. For example, the first control circuit 310 may extract an image of a cell or a group of cells included in the sample 500, calculate the number of cells or cell groups, and specify the pH of the culture medium, or the like based on the obtained image.

<Observation Apparatus>

The transparent plate 102 disposed on a part of the upper surface of the housing 101 of the observation apparatus 100 is formed of a transparent member having optically transparent characteristics, such as glass. The sample 500 is placed motionless on the transparent plate 102. As described above, the upper surface of the housing 101 is an arrangement surface on which the sample 500 is arranged.

The image acquisition unit 150 provided inside the housing 101 includes the imaging unit 151 and the internal illumination unit 155. The imaging unit 151 and the internal illumination unit 155 are fixed to the support unit 165, and move integrally as hereinafter described.

As shown in FIG. 2, the internal illumination unit 155 includes a first illumination optical system 156 and a first light source 157. The illumination light emitted from the first light source 157 is applied to the sample 500 via the first illumination optical system 156. The first light source 157 includes, for example, a light emitting diode (LED). The imaging unit 151 includes an imaging optical system 152 and an image sensor 153. The imaging unit 151 generates image data based on an image formed on the imaging area of the image sensor 153 via the imaging optical system 152. The imaging optical system 152 has a focus lens, and can change a focus position in the Z-axis direction. Further, it is preferable that the imaging optical system 152 be a zoom optical system that can change a focal length. The imaging unit 151 performs imaging in the direction of the sample 500, that is, the Z-axis direction, and acquires an image of the sample 500.

Figure 3:
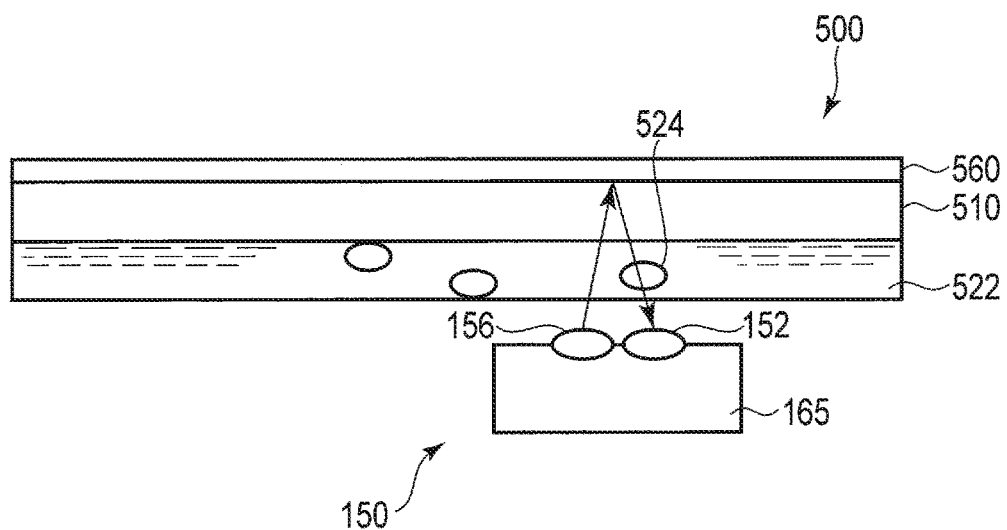
FIG. 3 is a schematic diagram for explaining observation of a sample by an image acquisition unit according to the one embodiment.

FIG. 3 is a schematic diagram schematically illustrating a configuration example of the image acquisition unit 150 and the sample. As shown in this figure, the illumination light emitted from the first illumination optical system 156 provided at the support unit 165 passes through a culture medium 522 and the like in the sample 500, hits an upper surface 560 of a vessel 510 of the sample 500 such as a lid or an upper surface, and is reflected by the upper surface 560. The reflected light illuminates cells 524 and the like in the culture medium 522 and enters the imaging optical system 152. The imaging unit 151 performs an imaging operation on the light incident on the imaging optical system 152. The image acquired with illumination by the internal illumination unit 155 in this manner is referred to as a first image.

Explanation of the configuration of the observation system 1 continues by referring back to FIGS. 1 and 2. The observation apparatus 100 includes a driving mechanism 160. The driving mechanism 160 includes an X-axis driving mechanism 162 including, for example, a feed screw and an actuator for moving the support unit 165 in the X-axis direction, and a Y-axis driving mechanism 164 including, for example, a feed screw and an actuator for moving the support unit 165 in the Y-axis direction. As described above, the imaging position in the Z-axis direction is changed by changing the position of the focus lens of the imaging optical system 152. Note that, instead of or in addition to the focus lens, the driving mechanism 160 may include a Z feed screw and a Z actuator for moving the support unit 165 in the Z-axis direction.

The observation apparatus 100 repeatedly performs imaging using the imaging unit 151 while changing the position of the image acquisition unit 150 in the X direction and the Y direction using the driving mechanism 160, and acquires a plurality of images at different positions. The observation apparatus 100 may combine these images to generate an image representing a single broad extent.

Furthermore, the observation apparatus 100 may repeatedly perform imaging while changing the imaging position in the Z-axis direction and similarly changing the position in the X direction and the Y direction, combine the images, and sequentially acquire images at the respective Z-direction positions. In this way, the images of each part may be three-dimensionally obtained.

The observation apparatus 100 further includes a second control circuit 110, an image processing circuit 120, a second storage circuit 130, and a second communication device 140. The second communication device 140 is a communication device for performing communication with the control apparatus 300.

The second storage circuit 130 stores, for example, programs and various control parameters used in each unit of the observation apparatus 100, movement patterns of the image acquisition unit 150, and the like. Further, the second storage circuit 130 stores data and the like obtained by the observation apparatus 100.

The image processing circuit 120 performs various types of image processing on the image data obtained by the imaging unit 151. The data after the image processing by the image processing circuit 120, for example, is stored in the second storage circuit 130 or transmitted to the control apparatus 300. Further, the image processing circuit 120 may perform various analyses based on the obtained images. For example, the image processing circuit 120 may extract an image of cells or cell groups contained in the sample 500, calculate the number of cells or cell groups, and specify the pH of the culture medium 522, etc. based on the obtained images. The analysis result thus obtained is also stored in the second storage circuit 130 or transmitted to the control apparatus 300, for example.

The second control circuit 110 controls the operation of each unit included in the observation apparatus 100. The second control circuit 110 controls the operation of the driving mechanism 160 to control the position of the image acquisition unit 150, controls the imaging operation of the imaging unit 151, controls the operation of the internal illumination unit 155, manages communication with the control apparatus 300 via the second communication device 140, and controls storing of data obtained by the observation apparatus 100.

<Illumination Apparatus>

The illumination apparatus 200 is an illumination apparatus that is provided on, for example, an inner wall in the incubator 400 and illuminates the sample 500 provided on the observation apparatus 100 as described above. The illumination apparatus 200 can be arranged at various positions in the incubator 400 that enable illuminating the sample 500. The illumination apparatus 200 may, for example, be disposed on a ceiling of the incubator 400, may be disposed on a side wall of the incubator 400, or may be disposed on or above the vessel 510 of the sample 500. The illumination apparatus 200 includes an external illumination unit 210, a third control circuit 230, and a third communication device 240.

The external illumination unit 210 includes a second light source 217 and a second illumination optical system 216. The second light source 217 includes, for example, an LED. The second light source 217 may be a light source that emits white illumination light or, for example, a light source that can individually emit red light, green light, and blue light depending on the configuration of the imaging unit 151 of the observation apparatus 100. The second illumination optical system 216 is configured to emit the illumination light from the second light source 217 in the direction of the sample 500. The sample 500 illuminated by the external illumination unit 210 is also imaged by the imaging unit 151 of the observation apparatus 100.

The image acquired with illumination by the external illumination unit 210 in this manner is referred to as a second image. The second image is a color image. That is, a user can grasp the color of the sample 500 based on the second image. Further, based on the second image, the transmittance of the sample 500 for each color can be calculated. For example, when the culture medium 522 contained in the sample 500 contains a dye such as phenol red, the color of which changes depending on the pH (hydrogen ion exponent), the pH can be calculated based on the light transmittance for each color.

The third communication device 240 communicates with the control apparatus 300 to receive an operation command from the control apparatus 300, and to transmit information relating to the status of the illumination apparatus 200 to the control apparatus 300. The third control circuit 230 controls the operation of each unit of the illumination apparatus 200 based on the command acquired from the control apparatus 300.

The image processing circuit 120, the first control circuit 310, the second control circuit 110, and the third control circuit 230 each include an integrated circuit such as a Central Processing Unit (CPU), an Application Specific Integrated Circuit (ASIC), a Field Programmable Gate Array (FPGA), or a Graphics Processing Unit (GPU). Each of the image processing circuit 120, the first control circuit 310, the second control circuit 110, and the third control circuit 230 may be configured by a single integrated circuit or the like, or may be configured by combining a plurality of integrated circuits or the like. Further, the second control circuit 110 and the image processing circuit 120 may together be configured by one integrated circuit or the like. The operations of these integrated circuits can be performed in accordance with programs stored in, for example, the first storage circuit 330, the second storage circuit 130, or the integrated circuits. The first storage circuit 330 and the second storage circuit 130 may include one or more of a non-volatile memory such as a flash memory, and a volatile memory such as a static random access memory (SRAM) or a dynamic random access memory (DRAM).

<Variations in System Configuration>

(Example of Control and Calculation)

The operation control of the observation apparatus 100 and the illumination apparatus 200 may be performed by the first control circuit 310 of the control apparatus 300, or the control apparatus 300 may only send commands and the second control circuit 110 of the observation apparatus 100 and the third control circuit 230 of the illumination apparatus 200 may perform the control.

The image processing may be performed by the image processing circuit 120 of the observation apparatus 100, or may be performed by the first control circuit 310 of the control apparatus 300 and/or the second control circuit 110 of the observation apparatus 100.

For example, for an analysis of calculating the pH, the first control circuit 310 of the control apparatus 300 may perform the analysis as an analysis circuit, or the second control circuit 110 of the observation apparatus 100 may perform the analysis as an analysis circuit. Further, a dedicated analysis circuit for analysis may be provided in the control apparatus 300 or the observation apparatus 100.

Figure 4:
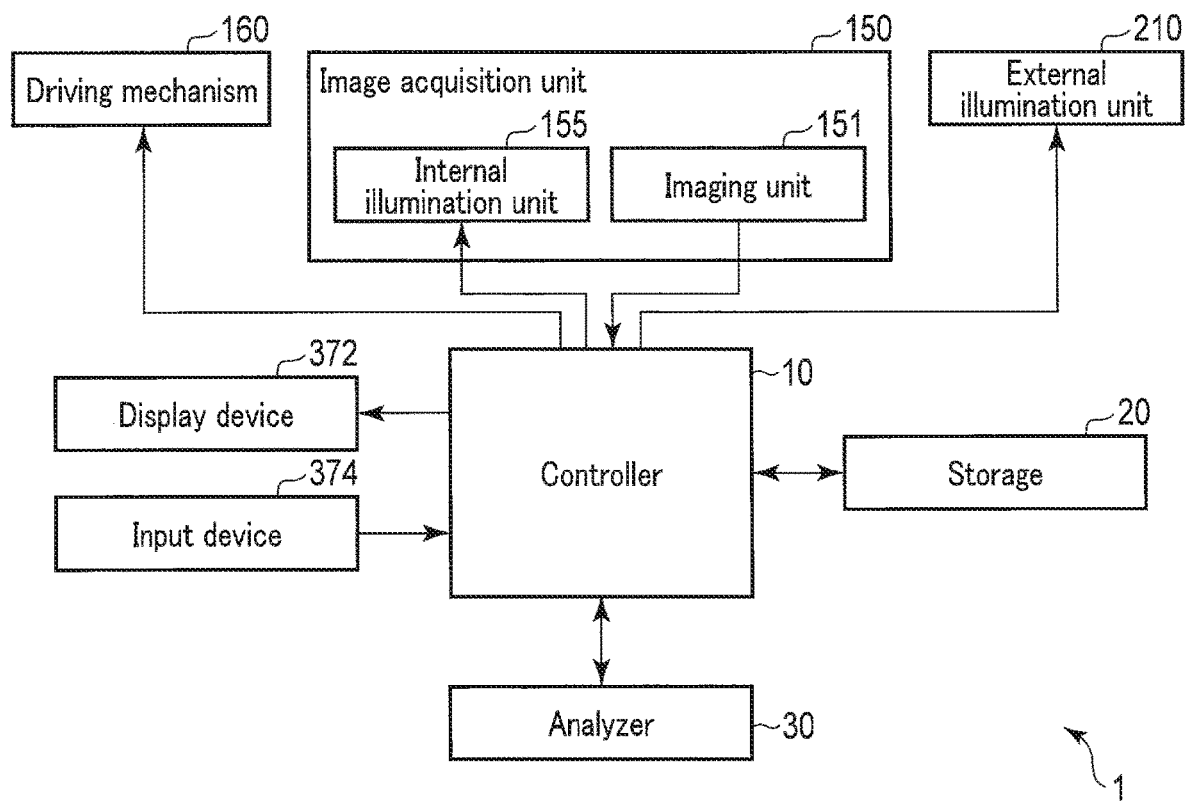
FIG. 4 is a diagram schematically illustrating an entire functional configuration example of an observation system according to the one embodiment.

As described above, since various controls and various analyses may be performed by either the control apparatus 300 or the observation apparatus 100, the entire functional configuration of the observation system 1 is as shown in FIG. 4. That is, the observation system 1 includes a controller 10 that controls operations of the image acquisition unit 150 including the internal illumination unit 155 and the imaging unit 151, the driving mechanism 160, the external illumination unit 210, and so on. The controller 10 controls, for example, the display of the display device 372 in order to present various information to the user, and acquires an input related to the operation of the observation system 1 by the user from, for example, the input device 374. The controller 10 causes an analyzer 30 to analyze the image and the like acquired by the imaging unit 151, and causes a storage 20 to store the acquired image, the analysis result, etc.

(Configuration Example of Illumination Apparatus and Imaging Unit)

Various combinations of the configuration of the external illumination unit 210 of the illumination apparatus 200 and the configuration of the imaging unit 151 are possible.

The second light source 217 of the external illumination unit 210 may serve as, for example, light sources of three colors of red, green, and blue, and the on/off and light intensity of a light source of each color can be controlled independently for each color. In this case, the image sensor 153 of the imaging unit 151 only needs to be able to acquire an image of a single color. That is, a monochrome sensor can be used for the image sensor 153. An image of each color can be obtained by controlling the respective light sources of each color of the second light source 217 in a time division manner and obtaining an image by the image sensor 153, which is adapted to obtain an image of only a single color, in a time division manner that is synchronous with the control of the second light source 217. As a result, the observation system 1 can acquire a color image and specify the pH of the culture medium 522 based on, for example, the color of the culture medium 522.

The second light source 217 of the external illumination unit 210 may also be, for example, a white light source, and its on/off and light intensity can be controlled. In this case, an image sensor 153 that can acquire a color image can be used as the image sensor 153 of the imaging unit 151. The image sensor 153 may be, for example, a color image sensor having sensor elements provided with color filters so as to be able to disperse light. The color filters can be arranged, for example, in a Bayer array for each pixel of the sensor. A color image can be obtained by imaging the sample 500 illuminated by the white second light source 217 using the imaging unit 151 having the color image sensor.

As described above, the imaging unit 151 is configured to be able to acquire images of at least three colors. For example, the pH of the culture medium 522 can be specified based on the color images.

Further, by configuring the imaging optical system so that an appropriate filter can be inserted into it and removed from it, the observation system 1 can take a configuration capable of acquiring, for example, a fluorescence image.

(Arrangement Example of Illumination Apparatus)

The illumination apparatus 200 including the external illumination unit 210 may be arranged at any position in the incubator 400 as long as it can illuminate the sample 500. For example, the illumination apparatus 200 may be arranged on the ceiling of the incubator 400 as shown in FIG. 1 or may be arranged on the side wall of the incubator 400. Further, the illumination apparatus 200 may be arranged, for example, on or above the vessel 510 of the sample 500 by making the shape of the illumination apparatus 200, for example, a plate.

(Example of System Configuration)

Several configuration examples of the observation system 1 will be described with reference to schematic diagrams shown in FIGS. 5A to 5F.

In the example shown in FIG. 5A, the illumination apparatus 200 is arranged on a ceiling 401 of the incubator 400. The second light source 217 of the external illumination unit 210 of the illumination apparatus 200 has light sources of three colors, a red light source 217R, a green light source 217G, and a blue light source 217B, and the light source of each color can be individually controlled. On the transparent plate 102 of the observation apparatus 100, a sample 500 is arranged in which a culture medium 522 and cells 524 are placed in a flask as a vessel 510. The illumination light emissions of three colors from the illumination apparatus 200 pass through the sample 500 and reach the image sensor 153 via the imaging optical system 152. The image sensor 153 is a monochrome image sensor. By performing imaging in synchronization with the time-division illumination by the illumination apparatus 200, an image of each color can be obtained.

As described with reference to FIG. 3, the illumination light emitted from the first light source 157 of the internal illumination unit 155 is reflected by the vessel upper surface 560 of the vessel 510 to illuminate the cells 524. Since the image sensor 153 is a monochrome image sensor, the obtained image of the cells 524 is also monochromatic. Generally, when observing cultured cells or the like, color information is often unnecessary. Therefore, by using, for example, red light, which is less likely to damage the cells 524, as the illumination light of the first light source 157, observation can be performed with less influence on the cells 524. Needless to say, when the first light source 157 includes multicolor light sources which can be individually controlled, different color images can also be obtained in a time division manner by this first light source 157.

In the example shown in FIG. 5A, the function of the controller 10 that controls the operations of the illumination apparatus 200, and of the image sensor 153 and the driving mechanism 160 of the observation apparatus 100, is performed by, for example, the first control circuit 310 of the control apparatus 300 outside the observation apparatus 100.

Figure 5B:
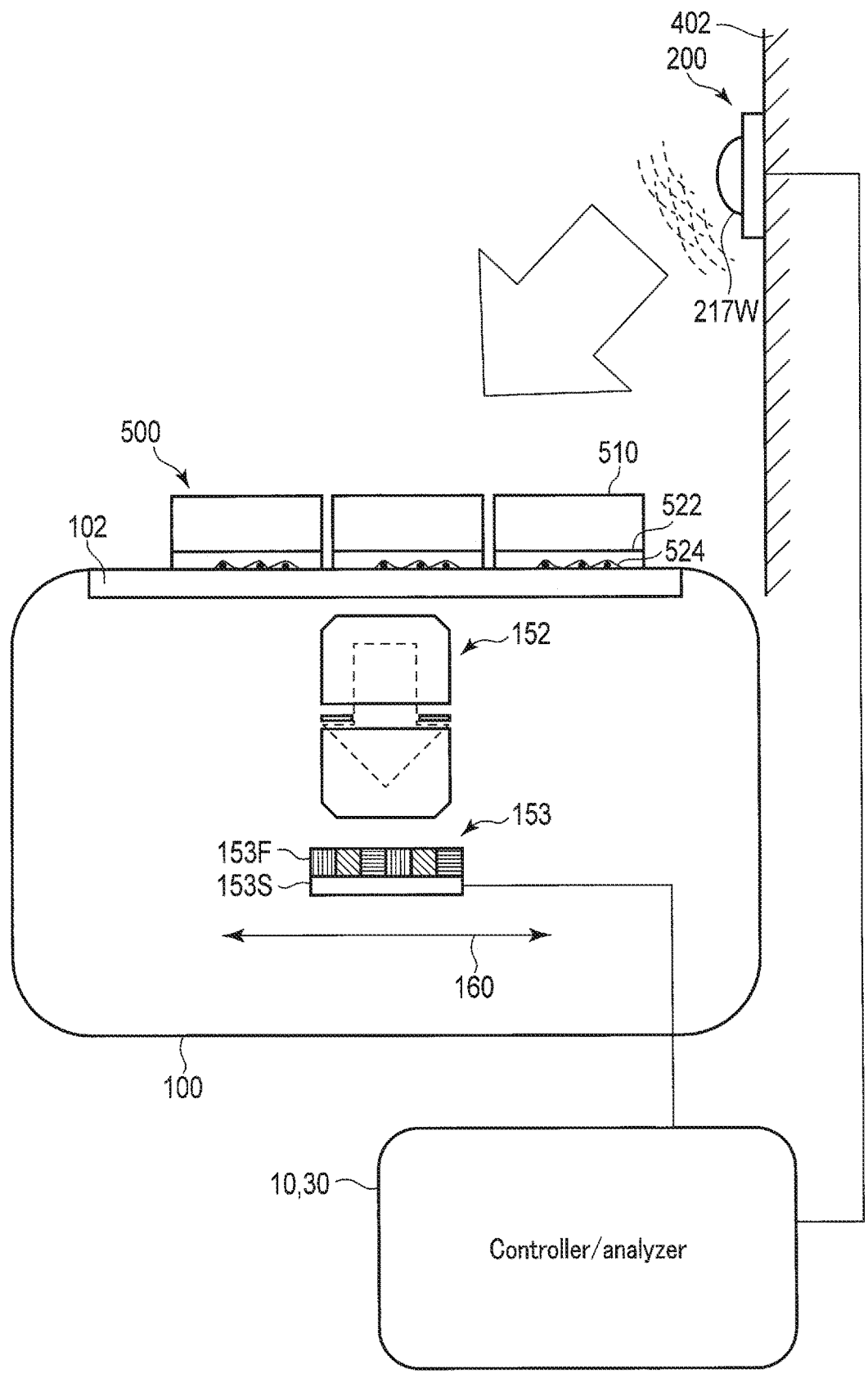
FIG. 5B is a diagram schematically illustrating an example of a variation of the configuration of the observation system according to the one embodiment.

In the example shown in FIG. 5B, the illumination apparatus 200 is arranged on a side wall 402 of the incubator 400. The second light source 217 of the external illumination unit 210 of the illumination apparatus 200 includes a white light source 217W that emits white light in which red, green, and blue light components are mixed. Samples 500 with a culture medium 522 and cells 524 in a petri dish as a vessel 510 are arranged on the transparent plate 102 of the observation apparatus 100. The white illumination light emitted from the illumination apparatus 200 passes through the sample 500 and reaches the image sensor 153 via the imaging optical system 152. The image sensor 153 is a color image sensor having a color filter 153F on a sensor 153S, and can capture a color image by imaging the sample 500 illuminated by the illumination apparatus 200.

As described with reference to FIG. 3, the illumination light emitted from the first light source 157 of the internal illumination unit 155 is reflected by the vessel upper surface 560 of the vessel 510 to illuminate the cells 524. Since the image sensor 153 is a color image sensor, for example, if a white light source is used as the first light source 157, the obtained image of the cells 524 is also a color image. Of course, if a monochrome light source is used as the first light source 157, an image of a color corresponding to the light source can be obtained using the image sensor 153.

In the example shown in FIG. 5B, the function of the controller 10 that controls the operations of the illumination apparatus 200, and of the image sensor 153 and the driving mechanism 160 of the observation apparatus 100, is performed by, for example, the first control circuit 310 of the control apparatus 300 outside the observation apparatus 100. The function of the analyzer 30 for estimating the pH of the culture medium 522 based on the obtained color image is also performed by, for example, the first control circuit 310 of the control apparatus 300 outside the observation apparatus 100.

Figure 5C:
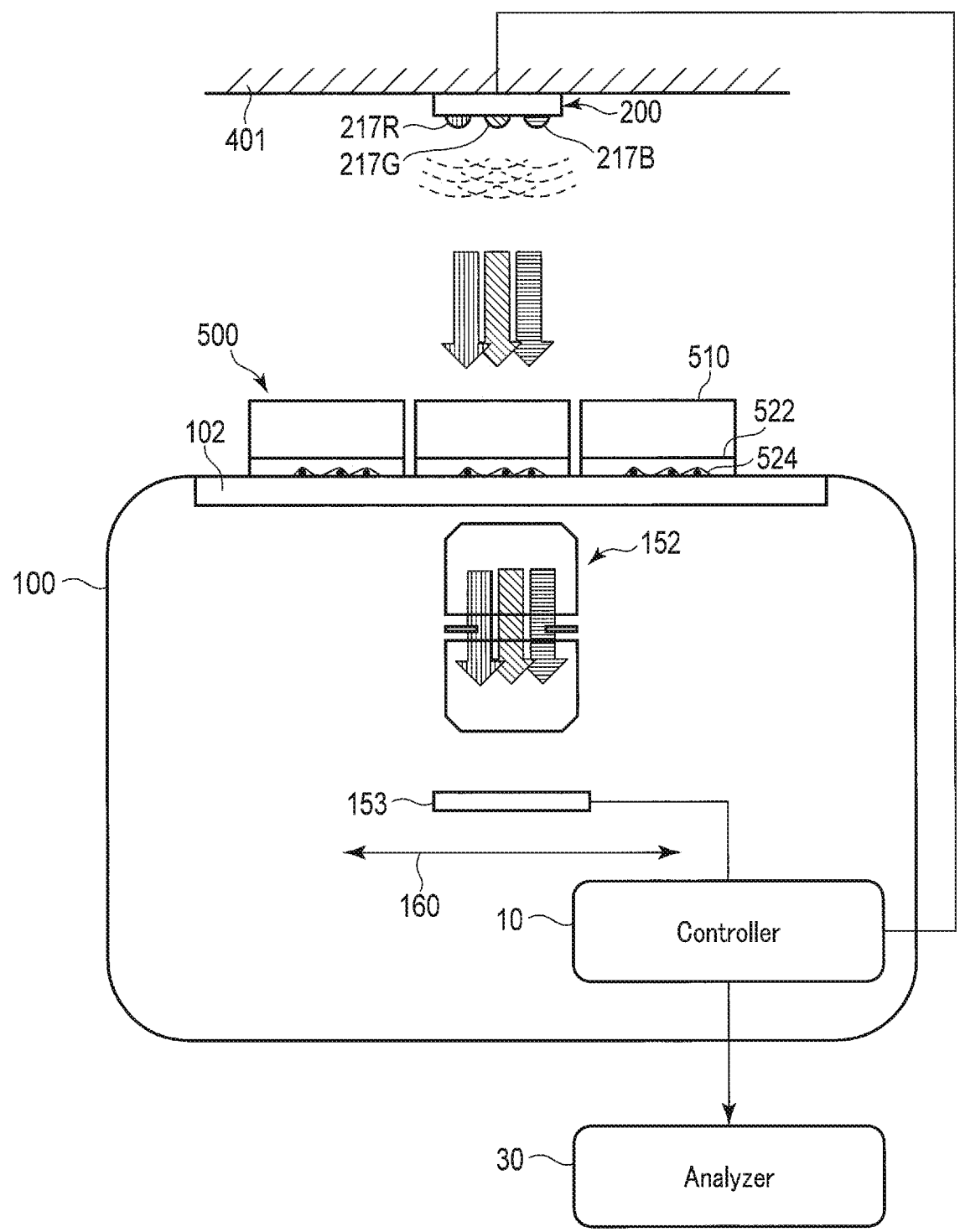
FIG. 5C is a diagram schematically illustrating an example of a variation of the configuration of the observation system according to the one embodiment.

In the example illustrated in FIG. 5C, the illumination apparatus 200 is arranged on the ceiling 401 of the incubator 400. The second light source 217 of the illumination apparatus 200 has light sources of three colors, the red light source 217R, the green light source 217G, and the blue light source 217B, and the light source of each color can be individually controlled. Samples 500 with a culture medium 522 and cells 524 in a petri dish as a vessel 510 are arranged on the transparent plate 102 of the observation apparatus 100. The illumination light emissions of three colors from the illumination apparatus 200 pass through the sample 500 and reach the image sensor 153 via the imaging optical system 152. The image sensor 153 is a monochrome image sensor. By performing imaging in synchronization with the time-division illumination by the illumination apparatus 200, an image of each color can be obtained.

In the example shown in FIG. 5C, the function of the controller 10 that controls the operations of the illumination apparatus 200, and of the image sensor 153 and the driving mechanism 160 of the observation apparatus 100, is performed by, for example, the second control circuit 110 in the observation apparatus 100. In addition, the function of the analyzer 30 that estimates the pH of the culture medium 522 based on the obtained color image is performed by, for example, the first control circuit 310 of the control apparatus 300 outside the observation apparatus 100.

Figure 5D:
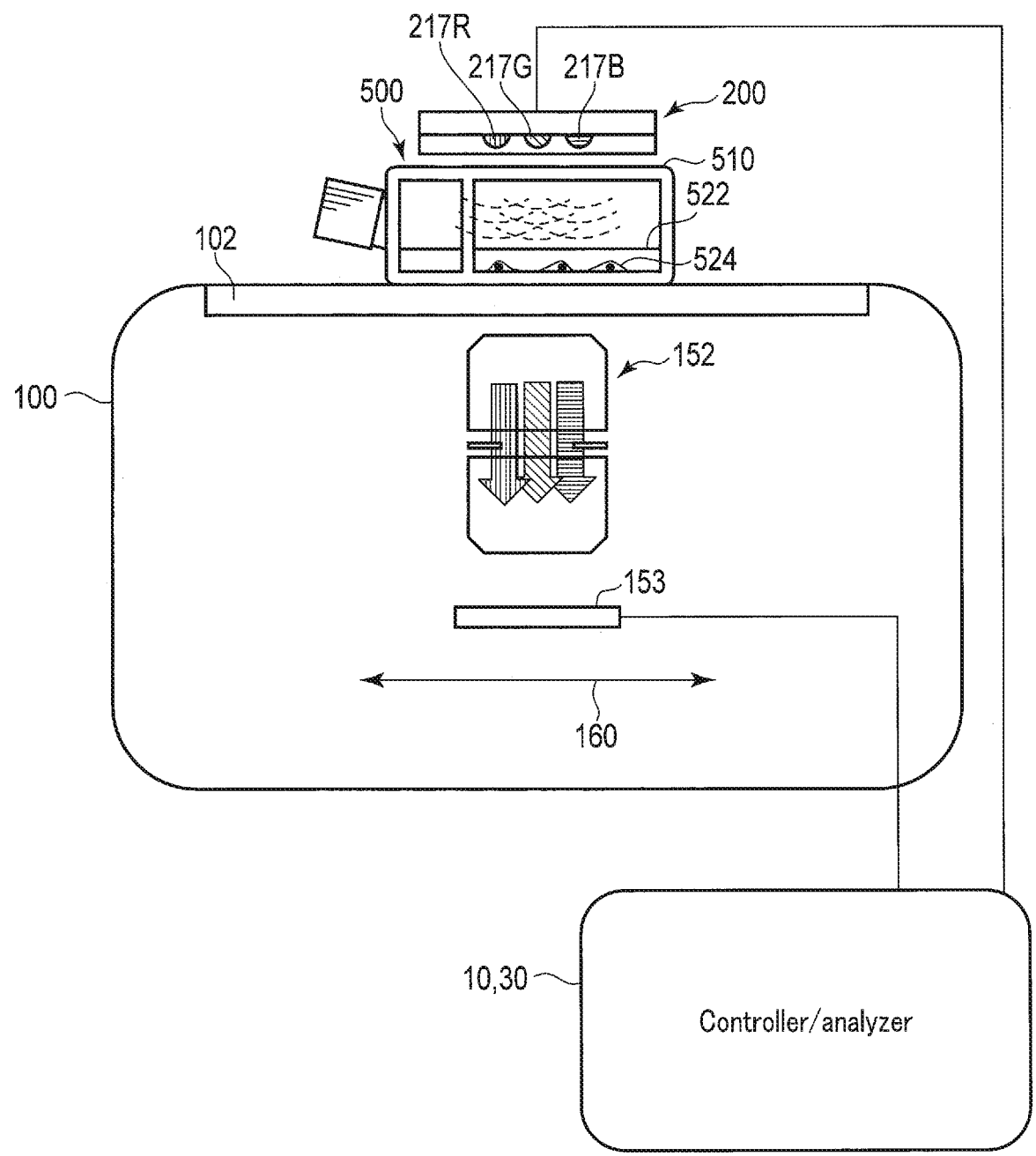
FIG. 5D is a diagram schematically illustrating an example of a variation of the configuration of the observation system according to the one embodiment.

In the example shown in FIG. 5D, a sample 500 with a culture medium 522 and cells 524 in a flask as a vessel 510 is placed on the transparent plate 102 of the observation apparatus 100. The illumination apparatus 200 is a plate-type illumination apparatus, and is arranged on or above the vessel 510. The second light source 217 of the illumination apparatus 200 has light sources of three colors, the red light source 217R, the green light source 217G, and the blue light source 217B, and the light source of each color can be individually controlled. The illumination light emissions of three colors from the illumination apparatus 200 pass through the sample 500 and reach the image sensor 153 via the imaging optical system 152. The image sensor 153 is a monochrome image sensor. By performing imaging in synchronization with the time-division illumination by the illumination apparatus 200, an image of each color can be obtained.

In the example shown in FIG. 5D, the function of the controller 10 that controls the operations of the illumination apparatus 200, and of the image sensor 153 and the driving mechanism 160 of the observation apparatus 100, is performed by, for example, the first control circuit 310 of the control apparatus 300 outside the observation apparatus 100. The function of the analyzer 30 for estimating the pH of the culture medium 522 based on the obtained color image is also performed by, for example, the first control circuit 310 of the control apparatus 300 outside the observation apparatus 100.

Figure 5E:
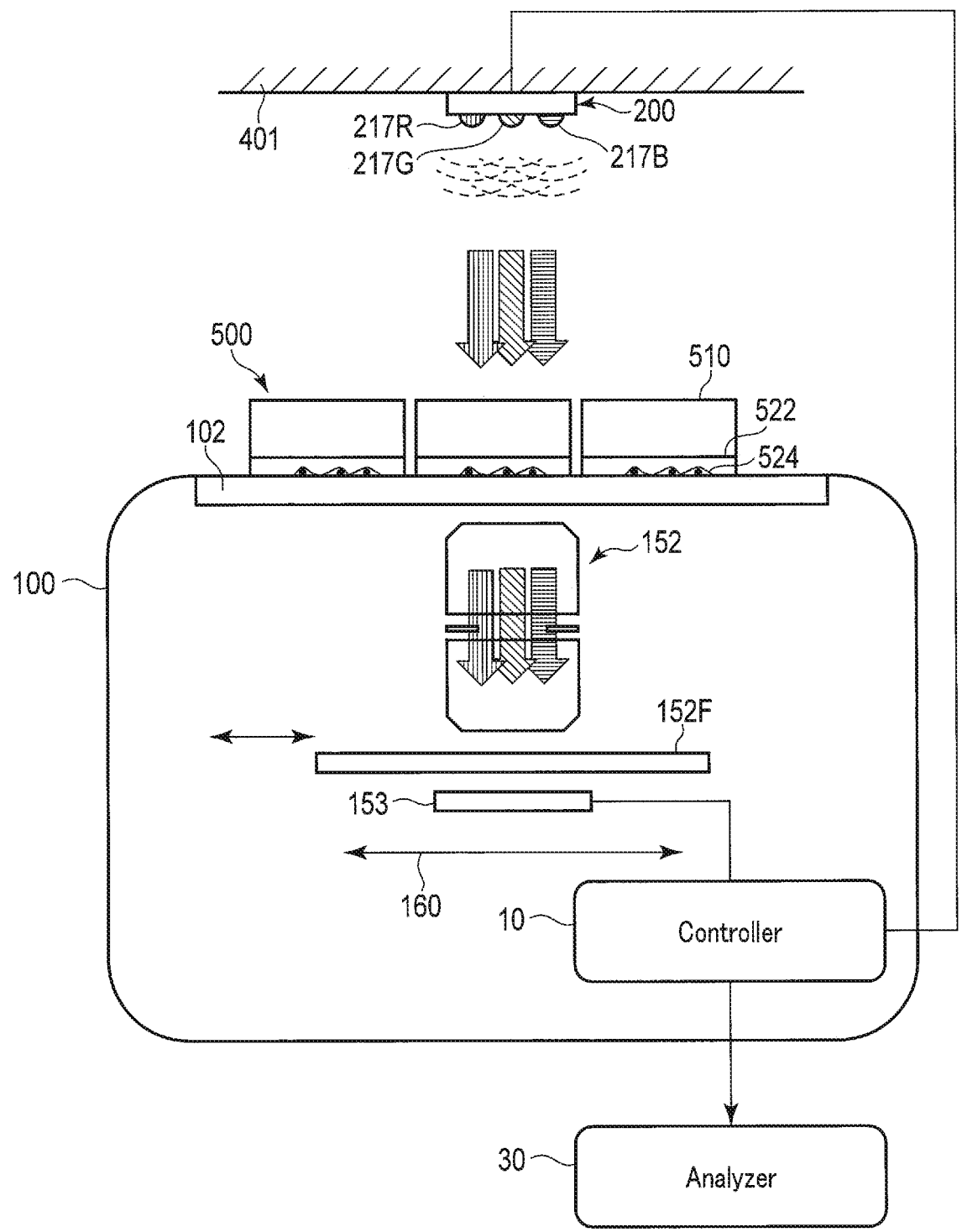
FIG. 5E is a diagram schematically illustrating an example of a variation of the configuration of the observation system according to the one embodiment.

In the example shown in FIG. 5E, the illumination apparatus 200 is arranged on the ceiling 401 of the incubator 400. The second light source 217 of the illumination apparatus 200 has light sources of three colors, the red light source 217R, the green light source 217G, and the blue light source 217B, and the light source of each color can be individually controlled. Samples 500 with a culture medium 522 and cells 524 in a petri dish as a vessel 510 are arranged on the transparent plate 102 of the observation apparatus 100. The illumination light emissions of three colors from the illumination apparatus 200 pass through the sample 500 and reach the image sensor 153 via the imaging optical system 152. The image sensor 153 is a monochrome image sensor. By performing imaging in synchronization with the time-division illumination by the illumination apparatus 200, an image of each color can be obtained. Further, the imaging optical system 152 is provided with a filter 152F for acquiring a fluorescence image. The filter 152F is inserted into or removed from the optical path of the imaging optical system 152. By inserting the filter 152F into the optical path and appropriately controlling the second light source 217, the observation apparatus 100 can acquire a fluorescence image. In addition, by removing the filter 152F from the optical path and appropriately controlling the second light source 217, the observation apparatus 100 can acquire a bright-field image.

Note that the acquisition of the fluorescence image using the filter 152F is not limited to the case where the second light source 217 of the external illumination unit 210 is used, and may be performed using the first light source 157 of the internal illumination unit 155.

In the example shown in FIG. 5E, the functions of the controller 10 that controls the operations of the illumination apparatus 200, and of the filter 152F, the image sensor 153, and the driving mechanism 160 of the observation apparatus 100, are performed by, for example, the second control circuit 110 in the observation apparatus 100. In addition, the function of the analyzer 30 that estimates the pH of the culture medium 522 based on the obtained color image is performed by, for example, the first control circuit 310 of the control apparatus 300 outside the observation apparatus 100.

Figure 5F:
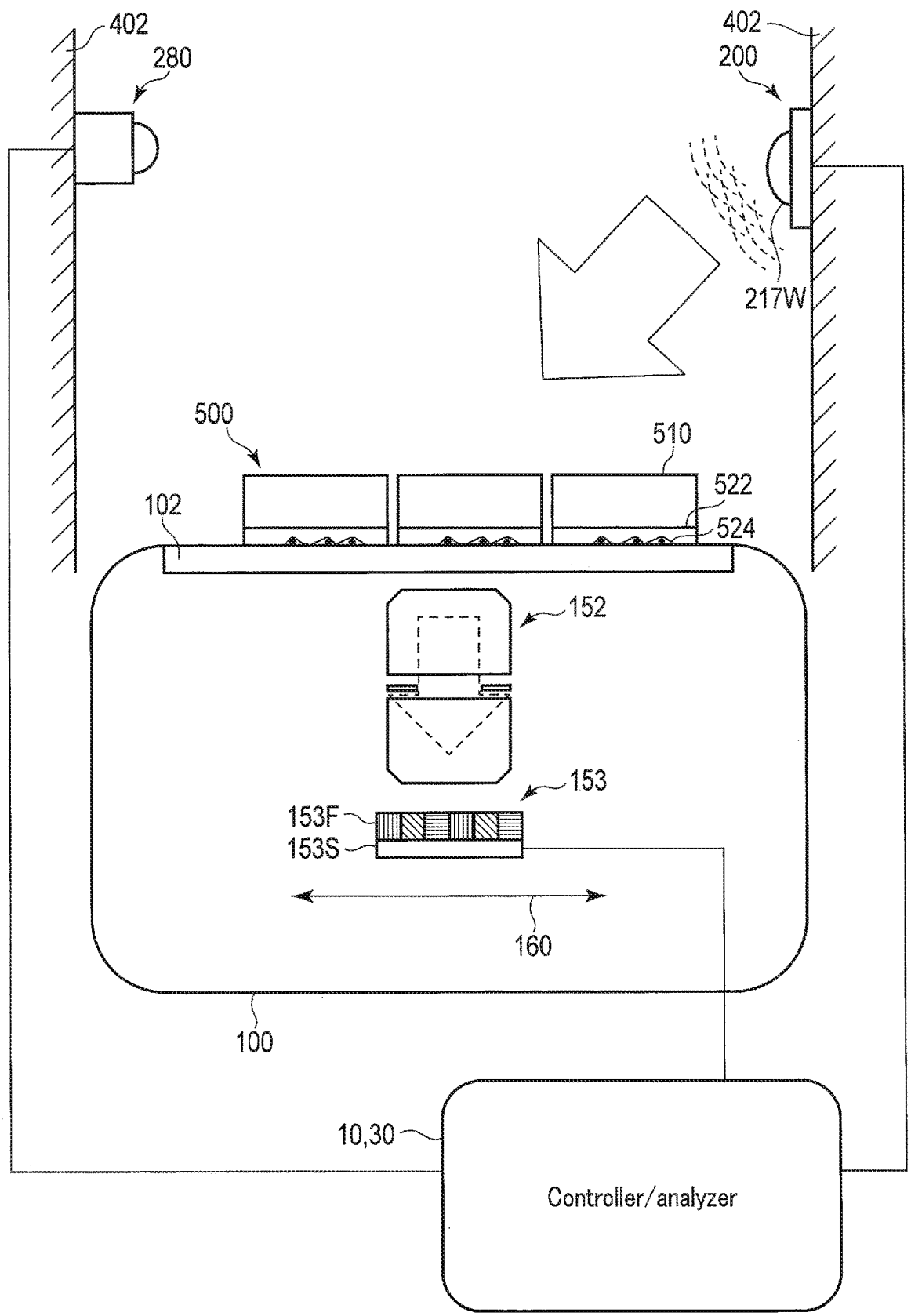
FIG. 5F is a diagram schematically illustrating an example of a variation of the configuration of the observation system according to the one embodiment.

In the example shown in FIG. 5F, the illumination apparatus 200 is arranged on the side wall 402 of the incubator 400. The second light source 217 of the illumination apparatus 200 includes the white light source 217W that emits white light in which red, green, and blue light components are mixed. Samples 500 with a culture medium 522 and cells 524 in a petri dish as a vessel 510 are arranged on the transparent plate 102 of the observation apparatus 100. The white illumination light emitted from the illumination apparatus 200 passes through the sample 500 and reaches the image sensor 153 via the imaging optical system 152. The image sensor 153 is an image sensor having the color filter 153F on the sensor 153S, and can capture a color image by imaging the sample 500 illuminated by the illumination apparatus 200.

Further, in this example, an observation camera 280 is provided in the incubator 400. The observation camera 280 in the incubator simultaneously captures an image covering the entire sample 500. If the observation camera 280 in the incubator is used, the position of the sample 500 can be acquired, so that the positional relationship, etc. between the position where the image acquisition unit 150 is imaging and the position where the sample 500 is arranged can be understood. This positional relationship can also be used, for example, when acquiring a reference intensity, such as the luminance of an image acquired without the sample 500, which is necessary for pH calculation described later. Further, the light intensity obtained by the observation camera 280 in the incubator may be used as a reference intensity required for the pH calculation.

In the example shown in FIG. 5F, the function of the controller 10 for controlling the operations of the illumination apparatus 200, the observation camera 280 in the incubator, and the image sensor 153 and the driving mechanism 160 of the observation apparatus 100 is carried out by, for example, the first control circuit 310 of the control apparatus 300 outside the observation apparatus 100. The function of the analyzer 30 for estimating the pH of the culture medium 522 based on the obtained color image is also performed by, for example, the first control circuit 310 of the control apparatus 300 outside the observation apparatus 100.

[Operation of Observation System]

The operation of the observation system 1 will be described with reference to the flowchart shown in FIG. 6. This process is started, for example, after the observation apparatus 100 and the illumination apparatus 200 are installed in the incubator 400, and the sample 500 is placed on the transparent plate 102 of the observation apparatus 100. Here, the example where the observation system 1 has an observation mode, a measurement mode, and a pH measurement mode as its operation modes will be described. The observation mode is a mode in which the user operates the driving mechanism 160 and the image acquisition unit 150 using the input device 374 to display an image of a desired position of the sample 500 on the display device 372. The measurement mode is a mode in which the observation system 1 acquires and analyzes an image of a predetermined position at a preset timing. The pH measurement mode is a mode in which the observation system 1 acquires a color image of the culture medium 522 of the sample 500 and acquires the pH of the culture medium 522 based on the color of the culture medium 522. The observation system 1 may have only some of these modes, or may further have other modes. The selection of the mode by the user can be performed at any timing by using, for example, the input device 374.

In step S101, the controller 10 determines whether or not the observation mode has been selected. When the observation mode has been selected, the process proceeds to step S102. In step S102, the controller 10 acquires, from the input device 374, information related to an operation instruction input by the user. In step S103, the controller 10 controls the operations of the driving mechanism 160 and the internal illumination unit 155 based on the acquired user's instruction. That is, the controller 10 causes the driving mechanism 160 to move the position of the image acquisition unit 150 according to the user's instruction. In the observation mode, the sample 500 is illuminated by the internal illumination unit 155, and an image of the sample 500 is acquired. Therefore, the controller 10 controls turning on/off, brightness, and the like of the internal illumination unit 155 according to user's instructions.

In step S104, the controller 10 causes the imaging unit 151 to perform an imaging operation, and acquires image data obtained from the imaging unit 151. In step S105, the controller 10 causes the display device 372 to display an image based on the obtained image data as a live view image. The user can observe the state of the sample 500 at a desired position by adjusting the position of the image acquisition unit 150 while viewing the image displayed on the display device 372.

In the observation mode according to the present embodiment, the observation system 1 can acquire a high-quality image and store it in the storage 20 when the user desires. In step S106, the controller 10 determines whether or not an imaging instruction has been received from the user. If the instruction for imaging has not been received, the process proceeds to step S108. On the other hand, when the imaging instruction is received, the process proceeds to step S107. In step S107, the controller 10 causes the imaging unit 151 to perform imaging in which a high-quality image is obtained, and stores the obtained image in the storage 20. Thereafter, the process proceeds to step S108.

In step S108, the controller 10 determines whether or not to end the observation mode. For example, the observation mode is terminated based on a user's instruction. If the observation mode is not to be terminated, the process returns to step S102, and the processes of steps S102 to S107 described above are repeated. On the other hand, when the observation mode is terminated, the process returns to step S101.

If it is determined in step S101 that the observation mode has not been selected, the process proceeds to step S109. In step S109, the controller 10 determines whether or not the measurement mode has been selected. When the measurement mode has been selected, the process proceeds to step S110.

In step S110, the controller 10 determines whether or not it is time to perform measurement. In the present embodiment, the observation system 1 can repeatedly acquire an image at a predetermined time or at a predetermined timing, for example, every hour, and perform analysis based on the image. In this way, the observation system 1 may, for example, obtain time-lapse images of the sample 500 in a predetermined range. If it is not the time to perform the measurement, the process repeats step S110 as a standby state. On the other hand, if it is time to perform the measurement, the process proceeds to step S111.

In step S111, the controller 10 controls the operations of the driving mechanism 160, the internal illumination unit 155, and the imaging unit 151 to image a predetermined position of the sample 500 under predetermined conditions. For example, when it is set that an image of an area of the sample 500 is to be acquired, the controller 10 controls the driving mechanism 160 to move the position of the image acquisition unit 150 within the area so that the images of the aforementioned area are sequentially taken by the imaging unit 151.

In step S112, the controller 10 causes the analyzer 30 to perform a predetermined analysis or the like based on the image(s) obtained by imaging. The analyzer 30 synthesizes a plurality of obtained images, for example, to create one synthesized image indicating a state of a predetermined area. The analyzer 30, for example, counts the number of cells and the like and specifies the size of a colony based on the obtained image(s). In step S113, the controller 10 stores the obtained image(s) and the analysis result in the storage 20.

In step S114, the controller 10 determines whether or not to terminate the measurement mode. For example, when a predetermined series of image acquisition and analysis is completed, it is determined to terminate the measurement. If the measurement mode is not to be ended, the process returns to step S110, and the processes of steps S110 to S113 described above are repeated. On the other hand, when ending the measurement mode, the process returns to step S101.

If it is determined in step S109 that the measurement mode has not been selected, the process proceeds to step S115. In step S115, the controller 10 determines whether or not the pH measurement mode has been selected. When the pH measurement mode has been selected, the process proceeds to step S116.

In step S116, the controller 10 controls the operations of the driving mechanism 160, the external illumination unit 210, and the imaging unit 151. That is, the driving mechanism 160 moves the image acquisition unit 150 to a position where the culture medium 522 of the sample 500 can be imaged. The controller 10 acquires a color image by synchronizing the illumination by the external illumination unit 210 and the imaging by the imaging unit 151. For example, when the external illumination unit 210 is configured to sequentially emit illumination light of three colors and the imaging unit 151 can acquire a single color image, the following operation is performed. That is, the controller 10 causes the external illumination unit 210 to sequentially emit illumination light of three colors, and causes the imaging unit 151 to image the culture medium 522 while the illumination light of each color is emitted. In this way, the controller 10 can acquire images of the respective colors for the culture medium 522. Further, for example, when the external illumination unit 210 can emit white light and the imaging unit 151 can acquire a color image, the following operation is performed. That is, the controller 10 causes the external illumination unit 210 to emit white light, and causes the imaging unit 151 to image the culture medium 522 while the white light is emitted. In this manner, the controller 10 can obtain a color image of the culture medium 522.

In step S117, the controller 10 performs an analysis for specifying the pH of the culture medium 522 based on the obtained image of each color or the color image related to the culture medium 522. For example, the color of the culture medium with phenol red added changes according to the pH. The pH can be specified based on this color.

For example, Jpn. Pat. Appln. KOKAI Publication No. S62-115297 discloses that the following relationship is established. That is, assuming that the absorbance values at wavelengths of 430 nm, 558 nm, and 630 nm are $A_{430}$, $A_{558}$ and $A_{630}$, respectively, $pH_0$, $pH_{10}$, and $pH_{20}$, which are the pH values of the respective Dulbecco MEM media each containing 0.001% phenol red and respectively having fetal bovine serum concentrations of 0%, 10%, and 20%, are represented by the following equations:

$$pH_0 = \log\left(\frac{A_{430} - A_{630}}{A_{558} - A_{630}}\right) \times 1.08 + 7.31$$

$$pH_{10} = \log\left(\frac{A_{430} - A_{630}}{A_{558} - A_{630}}\right) \times 1.15 + 7.38$$

-continued $$pH_{20} = \log\left(\frac{A_{430} - A_{630}}{A_{558} - A_{630}}\right) \times 1.27 + 7.47$$

Similarly, assuming that the absorbance values at wavelengths of 441 nm, 578 nm, and 634 nm are $A_{441}$, $A_{578}$, and $A_{634}$, respectively, the pH value of the Dulbecco MEM medium containing 0.001% phenol red and 10% fetal bovine serum is expressed by the following equation:

$$pH = \log\left(\frac{A_{441} - A_{634}}{A_{578} - A_{634}}\right) \times 1.19 + 7.86$$

It has peen shown that such a relationship can be equally obtained from performing measurement using a filter having a half-value width and from performing measurement using light of a single wavelength.

Also in the analysis of step S117 of the present embodiment, the pH of the culture medium 522 can be specified using the acquired image with reference to the above-described relationship determined according to various conditions, including, for example, the configuration of the observation system 1 such as the wavelength for the obtained image, the condition of the sample 500, and the like.

Based on the image of each color, the transmittance of the culture medium 522 for the light of each color is obtained. Here, the intensity of each color of light that has not passed through the sample 500, which is used as a reference intensity for calculating the transmittance, may be obtained in advance of arranging the sample 500. By comparing such a reference intensity with an image obtained by imaging the sample 500, the transmittance for each color can be obtained. Further, even in a state where the sample 500 is disposed on the transparent plate 102, the reference intensity can be set based on an image captured by the imaging unit 151 at a position without the sample 500, to which the driving mechanism 160 has moved the imaging unit 151. In particular, in a configuration in which the attachment position of the illumination apparatus 200 can be changed, the reference intensity can be changed according to the position or the like of the illumination apparatus 200, and therefore it is preferable to acquire the reference intensity for each instance of attachment of the illumination apparatus 200.

In addition, the reference intensity is not limited to the use for obtaining the transmittance when measuring the pH, and may be used, for example, when correcting the color information of the obtained image in comparison with the transmittance and color data prepared in advance.

In step S118, the controller 10 causes the display device 372 to display the obtained pH value. By utilizing the pH measurement mode as described above, the user can know the pH of the culture medium 522 of the sample 500. Thereafter, the process returns to step S101, and the above-described process is repeated.

Note that the pH measurement mode may be executed based on a user's instruction, or may be repeatedly executed over time according to a predetermined schedule. Such execution over time allows monitoring a change of pH over time.

If it is determined in step S115 that the pH measurement mode has not been selected, the process proceeds to step S119. In step S119, the controller 10 determines whether or not to terminate the processing. For example, when the user inputs the cessation of using the observation system 1, it is determined to be finished. If it is determined that the processing is not to be terminated, the process returns to step S101, and the above-described processing is repeated. When it is determined to be finished, the series of processing is terminated.

According to the observation system 1 of the present embodiment as described above, the sample 500 set in the incubator 400 can be observed, recorded, and subjected to various analyses as it is. At this time, appropriate information can be obtained by properly using the internal illumination unit 155 and the external illumination unit 210 as the illumination light sources. The configuration of the external illumination unit 210 can be appropriately changed as needed.

Generally, when observing cultured cells or the like, color information is unnecessary. Therefore, by making the image sensor 153 of the imaging unit 151 a monochrome sensor, a high-resolution image can be obtained at low cost. On the other hand, when it is desired to measure the pH of the culture medium 522 or the like, the pH of the culture medium 522 can be measured based on the image as described above by using an external illumination unit 210 that emits light having a wavelength optimal for the measurement of the pH, even if the imaging unit 151 having a monochrome sensor is used.

In addition, by using the external illumination unit 210, the transmitted light can be easily measured using the imaging unit 151. Further, according to the observation system 1, no special vessel or the like is required for measuring the transmitted light. According to the illumination by the external illumination unit 210, the influence of heat on the sample 500 can be reduced and the size of the observation apparatus 100 can be reduced as compared with the case where the internal illumination unit 155 is used.

Further, the observation system 1 is configured to be able to acquire images of three colors as in the above-described embodiment, so that it is possible to acquire a full-color image of the sample 500 or the like, and it is also possible to specify the pH with high accuracy. The user can also quickly determine the pH of the culture medium 522 by looking at the color image of the culture medium 522 without the analysis by the analyzer 30.

Among the techniques described in the embodiments, the control mainly described in the flowchart can be realized using a program. This program can be stored in a storage medium or the storage. There are various methods of storing the program in the storage medium or the storage, and the storing may be performed at the time of product shipment, may be performed using a distributed storage medium, or may be performed using downloading via the Internet. Further, all or a part of the above-described processing may be, for example, performed using artificial intelligence, etc. constructed using deep learning.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An observation system comprising:
an observation apparatus including a housing having an arrangement surface for placement of a sample including a culture medium; and
an external light source disposed outside the housing, the external light source being configured to emit external illumination light,
an internal light source provided in the housing, the internal light source being configured to emit internal illumination light; wherein
at least a part of the arrangement surface is formed of an optically transparent member, and
the observation apparatus includes an image sensor provided in the housing, the image sensor configured to image, via the optically transparent member, the sample illuminated by the external illumination light to acquire at least three monochrome images, each of the at least three monochrome images respectively corresponding to one of at least three different colors of the visible spectrum; and
the image sensor is configured to image, via the optically transparent member, the sample illuminated by the internal illumination light to acquire a first image, and the image sensor being further configured to acquire the at least three monochrome images illuminated by the external light source as a second image.

2. The observation system according to claim 1, further comprising a controller configured to
for obtaining the first image, cause the internal light source to emit the internal illumination light, and to cause the image sensor to perform imaging, and
for acquiring the second image, cause the external light source to emit the external illumination light, and to cause the image sensor to perform imaging.

3. The observation system according to claim 2, wherein the controller is arranged inside the housing.

4. The observation system according to claim 2, wherein the controller is arranged outside the housing.

5. The observation system according to claim 1, further comprising a controller configured to calculate, for each of the at least three colors, a transmittance for light transmitted through the sample based on the at least three monochrome images of the at least three colors, and to calculate a pH of the culture medium included in the sample.

6. The observation system according to claim 5, wherein the controller is configured to:
acquire an intensity of light that is not transmitted through the sample as a reference intensity, and
calculate the pH based on the reference intensity.

7. The observation system according to claim 5, wherein the image sensor is configured to acquire the images of the at least three colors over time, and
the controller is configured to calculate the pH over time.

8. The observation system according to claim 1, wherein:
the external light source includes at least three light sources, each configured to independently emit illumination light of a different one of the at least three colors; and
the image sensor is a monochrome image sensor configured to acquire the at least three monochrome images in each of the at least three colors.

9. The observation system according to claim 1, wherein:
the external light source is a white light source; and
the image sensor is a color image sensor having a color filter such that the color image sensor acquires the at least three monochrome images.

10. An observation system comprising:
an observation apparatus including a housing having an arrangement surface for placement of a sample including a culture medium; and an external light source disposed outside the housing, the external light source being configured to emit external illumination light, wherein at least a part of the arrangement surface is formed of an optically transparent member, and the observation apparatus includes an image sensor provided in the housing, the image sensor configured to image, via the optically transparent member, the sample illuminated by the external illumination light to acquire at least three monochrome images, each of the at least three monochrome images respectively corresponding to one of at least three different colors of the visible spectrum; and the external light source includes at least three light sources, each configured to independently emit illumination light of a different one of the at least three colors, and the image sensor is configured to acquire the at least three monochrome images by respectively imaging the sample illuminated with the external illumination light corresponding to each of the at least three colors.

11. The observation system according to claim 10, wherein the image sensor includes a monochrome image sensor for acquiring the at least three monochrome images.

12. An observation system comprising:
an observation apparatus including a housing having an arrangement surface for placement of a sample including a culture medium; and an external light source disposed outside the housing, the external light source being configured to emit external illumination light, wherein at least a part of the arrangement surface is formed of an optically transparent member, and the observation apparatus includes an image sensor provided in the housing, the image sensor configured to image, via the optically transparent member, the sample illuminated by the external illumination light to acquire at least three monochrome images, each of the at least three monochrome images respectively corresponding to one of at least three different colors of the visible spectrum; and the external light source includes a light source configured to emit illumination light including at least three color components respectively corresponding to the at least three different colors, and the image sensor is configured to disperse the at least three color components, and to acquire the at least three monochrome images respectively corresponding to the at least three colors by imaging the sample illuminated with the at least three color components emitted from the external light source.

13. The observation system according to claim 12, wherein:
the external light source includes at least three light sources, each configured to independently emit illumination light of a different one of the at least three colors; and the image sensor is a monochrome image sensor configured to acquire the at least three monochrome images in each of the at least three colors.

14. The observation system according to claim 12, wherein:
the external light source is a white light source; and
the image sensor is a color image sensor having a color filter such that the color image sensor acquires the at least three monochrome images.

15. An observation system comprising:
an observation apparatus including a housing having an arrangement surface for placement of a sample including a culture medium; and an external light source disposed outside the housing, the external light source being configured to emit external illumination light, wherein at least a part of the arrangement surface is formed of an optically transparent member, the observation apparatus includes an image sensor provided in the housing, the image sensor configured to image, via the optically transparent member, the sample illuminated by the external illumination light to acquire at least three monochrome images, each of the at least three monochrome images being one of at least three different colors of the visible spectrum, respectively;

the observation apparatus is configured to be placed in an incubator, and the external light source is configured to be attached to an inner wall of the incubator.

16. The observation system according to claim 15, wherein:
the external light source includes at least three light sources, each configured to independently emit illumination light of a different one of the at least three colors; and the image sensor is a monochrome image sensor configured to acquire the at least three monochrome images in each of the at least three colors.

17. The observation system according to claim 15, wherein:
the external light source is a white light source; and
the image sensor is a color image sensor having a color filter such that the color image sensor acquires the at least three monochrome images.

18. An observation system comprising:
an observation apparatus including a housing having an arrangement surface for placement of a sample including a culture medium; and an external light source disposed outside the housing, the external light source being configured to emit external illumination light, wherein at least a part of the arrangement surface is formed of an optically transparent member, the observation apparatus includes an image sensor provided in the housing, the image sensor configured to image, via the optically transparent member, the sample illuminated by the external illumination light to acquire at least three monochrome images, each of the at least three monochrome images respectively corresponding one of at least three different colors of the visible spectrum;

the sample includes a culture vessel,
the observation apparatus is configured to be placed in an incubator, and the external light source is configured to be arranged above the culture vessel.

19. The observation system according to claim 18, wherein:
the external light source includes at least three light sources, each configured to independently emit illumination light of a different one of the at least three colors; and the image sensor is a monochrome image sensor configured to acquire the at least three monochrome images in each of the at least three colors.

20. The observation system according to claim 18, wherein:
the external light source is a white light source; and
the image sensor is a color image sensor having a color filter such that the color image sensor acquires the at least three monochrome images.

* * * * *